United States Patent [19]

Davis et al.

[11] Patent Number: 5,299,566
[45] Date of Patent: Apr. 5, 1994

[54] METHOD OF ADMINISTERING PHOSPHOLIPID DISPERSIONS

[75] Inventors: Craig W. Davis; Rodney G. Snyder, both of Greenville, N.C.

[73] Assignees: Burroughs Wellcome Co., Research Triangle Park, N.C.; The Wellcome Foundation LTD, London, United Kingdom

[21] Appl. No.: 948,144

[22] Filed: Sep. 18, 1992

[30] Foreign Application Priority Data

Sep. 19, 1991 [GB] United Kingdom ............... 912000

[51] Int. Cl.$^5$ .................... A61K 37/02; A61M 11/00
[52] U.S. Cl. .................... 128/200.24; 128/203.26; 128/200.14; 514/78
[58] Field of Search ............... 128/203.26, 203.27, 128/200.24, 204.17, 200.14; 514/78

[56] References Cited

U.S. PATENT DOCUMENTS

| | | | |
|---|---|---|---|
| 3,745,991 | 7/1973 | Gauthier et al. | 128/716 |
| 4,312,860 | 1/1982 | Clements | 514/78 |
| 4,659,805 | 4/1987 | Schilling | 530/350 |
| 4,826,821 | 5/1989 | Clements | 514/78 |
| 4,832,012 | 5/1989 | Raabe et al. | 128/200.21 |
| 4,905,685 | 3/1990 | Olsson et al. | 128/203.12 |
| 4,912,038 | 3/1990 | Schilling | 435/69.1 |
| 4,933,280 | 6/1990 | Schilling | 435/69.1 |
| 5,013,720 | 5/1991 | Whitsett | 514/12 |
| 5,032,585 | 7/1991 | Lichtenberger | 514/78 |
| 5,038,769 | 8/1991 | Krauser | 128/203.27 |
| 5,049,388 | 9/1991 | Knight | 424/450 |
| 5,057,502 | 10/1991 | Walsh | 514/54 |
| 5,134,129 | 7/1992 | Lichtenberger | 514/78 |

FOREIGN PATENT DOCUMENTS

| | | | |
|---|---|---|---|
| 2032421 | 4/1972 | Fed. Rep. of Germany | 128/203.27 |
| 2729768 | 1/1979 | Fed. Rep. of Germany | 128/203.27 |
| 3708945 | 9/1987 | Fed. Rep. of Germany | 128/203.26 |
| WO91/00871 | 1/1991 | PCT Int'l Appl. . | |
| 2130401 | 5/1984 | United Kingdom | 128/204.17 |

OTHER PUBLICATIONS

Venkitaraman et al., "Enhancement of Biophysical Activity of Lung Surfactant Extracts and Phospholipid Apoprotein Mixtures by Surfactant Protein A." *Chemistry & Physics of Lipids,* vol. 56(2–3), pp. 185–194, 1990.
Otto G. Raabe, et al., *Journal of Aerosol Medicine* 2, 201–210 (1989).

*Primary Examiner*—Edgar S. Burr
*Assistant Examiner*—Eric P. Raciti
*Attorney, Agent, or Firm*—Bell, Seltzer, Park & Gibson

[57] ABSTRACT

A method of administering a surfactant dispersion to the lungs of a patient in need of such treatment is disclosed. The method comprises heating the dispersion and nebulizing the heated dispersion to produce respirable surfactant particles. The respirable surfactant particles delivered to the lungs of the patient. By heating the dispersion the amount of phospholipid delivered to the lungs of the patient is increased.

The dispersion is comprised of a phospholipid dispersed in an aqueous carrier. In a particular embodiment of the invention, the phospholipid is preferably dipalmitoylphosphatidylcholine (DPPC) included in an amount from about 8 to 50 milligrams per milliliter of aqueous carrier, and the dispersion is preferably heated to a temperature between about 25° C. and 75° C.

36 Claims, 6 Drawing Sheets

3X SURFACTANT FORMULATION

Fig.5

6X SURFACTANT FORMULATION

Fig. 6

METHOD OF ADMINISTERING PHOSPHOLIPID DISPERSIONS

FIELD OF THE INVENTION

The present invention concerns methods for the administration of aerosolized surfactant formulations to the lungs of a patient.

BACKGROUND OF THE INVENTION

Respiratory distress syndrome (RDS), also termed hyaline membrane disease, is the leading cause of death and disability among premature infants. Of the 230,000 to 250,000 infants born prematurely each year in the United States, 40,000 to 50,000 develop RDS; and of those who develop this disease, 5,000 to 8,000 die. See generally R. Perelman and P. Farrell, *Pediatrics* 70, 570 (1982); D. Vidyasagar, in *Hyaline Membrane Disease: Pathogenesis and Pathophysiology*, 98 (L. Stern Ed. 1984). In addition, RDS can occur in children, adolescents, and adults as a result of trauma or other injury to the lungs. 150,000 cases of adult respiratory distress syndrome (ARDS) are reported annually, with 60–80% mortality. See American Lung Program, *Respiratory Diseases, Task Force Report on Problems, Research Approaches, and Needs*, National Heart and Lung Institute, DHEW Publn. (NIH) 73–432: 165–80 (1972).

RDS is caused by a primary deficiency in lung surfactant, a material ordinarily secreted onto the surface of lung alveoli. ARDS consists of a secondary deficiency in lung surfactant due to surfactant inhibition and/or decreased secretion. In the absence of surfactant, the alveoli tend to collapse during exhalation. Collapse can be avoided by mechanically ventilating the lungs. A problem with mechanical ventilation, however, is that it can cause damage to the lungs because of high oxygen concentrations and positive pressures.

A number of groups have sought to develop surfactant formulations which can be used to treat or prevent RDS and ARDS. Both human and bovine natural surfactants have been administered into the airways of human subjects. See, e.g., J. Horbar et al., *N. Eng. J. Med.* 320, 959 (1989); R. Soll et al., *Pediatric Res.* 23, 425A (1988). Problems with such natural surfactants are, however, potential contamination with microorganisms and potential sensitization of the patient to proteins therein. Accordingly, completely synthetic surfactants have been developed. See, e.g., U.S. Pat. No. 4,826,821 to Clements; U.S. Pat. No. 4,312,860 to Clements.

While the development of surfactant formulations have provided an alternative to mechanical ventilation alone, clinicians are now faced with the difficult problem of how to quickly and efficaciously administer these formulations to the lungs of patients. U.S. Pat. No. 4,832,012 to Raabe and Lee discloses a nebulizing apparatus which may be used to deliver drug-containing liquids to the lungs of patients in the form of an aerosol. It is suggested that the liquid can be heated or cooled prior to nebulization (column 4, lines 47–48). Raabe and Lee do not address the problems involved in administering surfactant formulations to the lungs of a patient. Such formulations are dispersions of lipids in an aqueous carrier solution, rather than single phase solutions.

In view of the foregoing, an object of the present invention is to provide a means for administering surfactant formulations to the lungs of patients in the form of an aerosol.

SUMMARY OF THE INVENTION

The present invention provides a method of administering a surfactant dispersion to the lungs of a patient in need of such treatment. The method comprises heating the dispersion to a temperature between about 25° C. and 90° C. The dispersion is comprised of a phospholipid dispersed in an aqueous carrier. The phospholipid is included in an amount from about 10 to 90 milligrams per milliliter of aqueous carrier. The dispersion is nebulized to produce respirable surfactant particles, and the respirable surfactant particles delivered to the lungs of the patient. By heating the dispersion prior to nebulization, the amount of phospholipid delivered to the lungs of the patient is increased.

BRIEF DESCRIPTION OF THE DRAWINGS

FIG. 5 shows total mg of DPPC collected from a nebulized 3× surfactant formulation maintained at temperatures ranging from 2° C. to 60° C.

FIG. 6 shows total mg of DPPC collected from a nebulized 6× surfactant formulation maintained at temperatures ranging from 2° C. to 60° C.

DETAILED DESCRIPTION OF THE INVENTION

Figure 1:
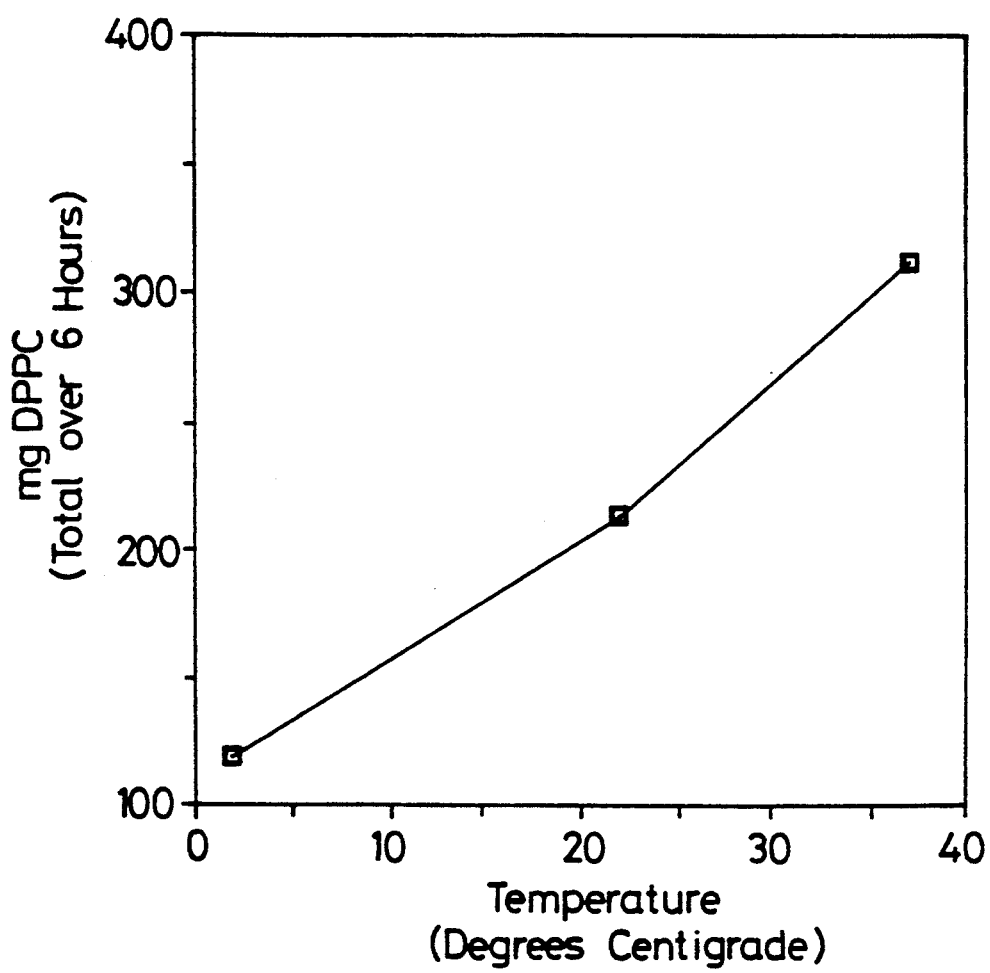
FIG. 1 shows milligrams (mg) of dipalmitoylphosphatidylcholine (DPPC) collected over six hours from a nebulized 1× surfactant formulation maintained at temperatures ranging from 2° Centigrade to 37° Centigrade.
Figure 2:
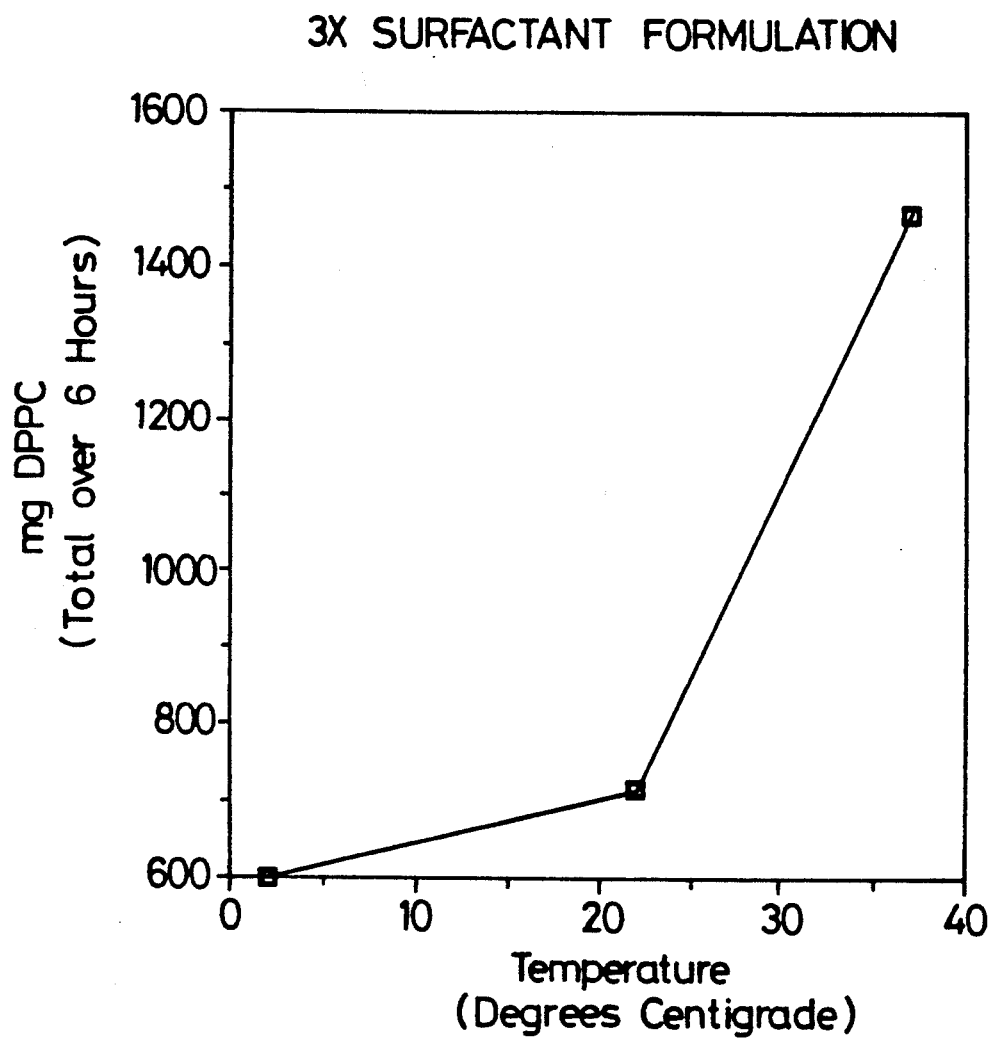
FIG. 2 shows mg of DPPC collected over a six hour period from a nebulized 3× surfactant formulation maintained at temperatures ranging from 2° C. to 37° C.
Figure 3:
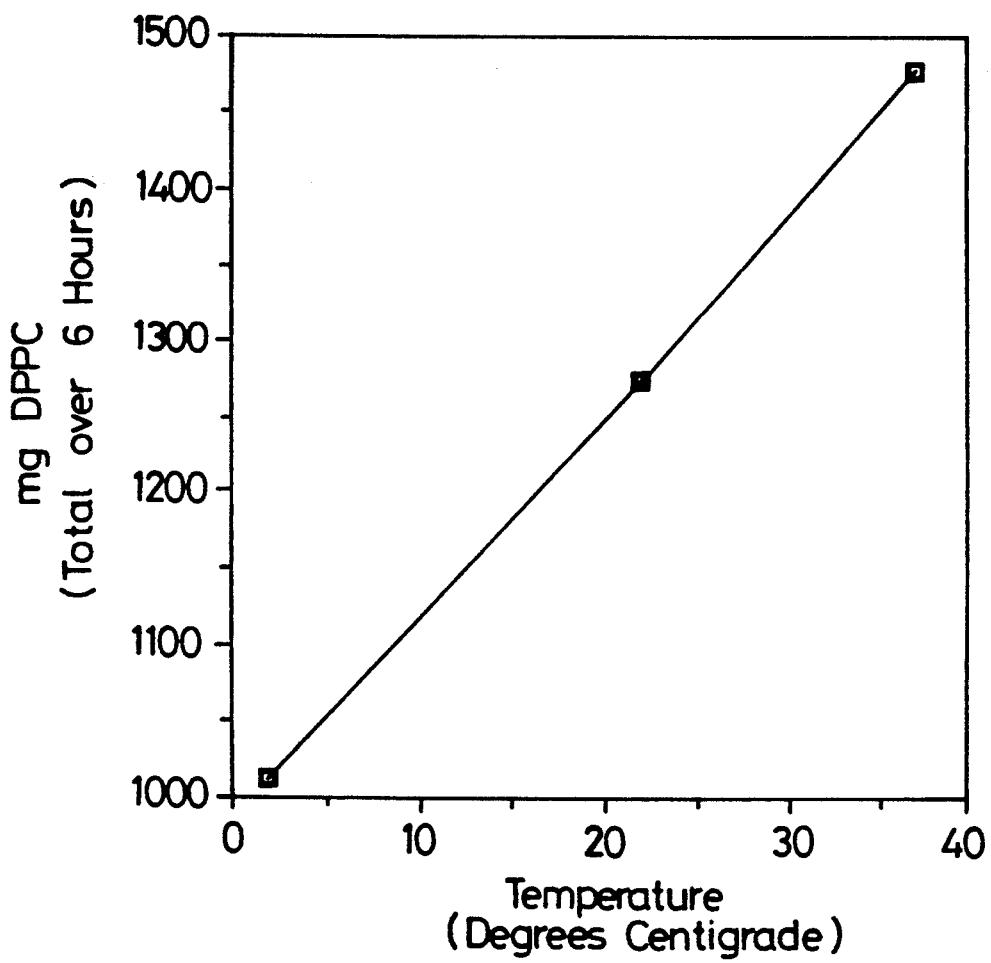
FIG. 3 shows mg of DPPC collected over a six hour period from a nebulized 6× surfactant formulation maintained at temperatures ranging from 2° C. to 37° C.

Surfactant formulations used in practicing the present invention may be of any type useful for the treatment of RDS or ARDS, whether of natural (i.e., human, bovine), see, e.g., J. Horbar et al., *N. Eng. J. Med.* 320, 959 (1989); R. Soll et al., *Pediatric Res.* 23, 425A (1988), recombinant, or synthetic origin, or combinations thereof. See, e.g., Y. Tanaka et al., *J. Lipid Res.* 27, No. 2, 475 (1986), T. Fujiwara et al., *Lancet* 1, 55 (Jan. 12, 1980) (cow-lung extract fortified with dipalmitoylphosphatidylcholine); U.S. Pat. No. 4,912,038 to Schilling et al. (recombinant DNA sequences encoding alveolar surfactant proteins). Particularly preferred for practicing the present invention is synthetic surfactant of the type described in U.S. Pat. No. 4,826,821 to Clements (Applicants specifically intend that the disclosure of all patent references cited herein be incorporated herein by reference). Also useful for practicing the present invention is synthetic surfactant of the type described in U.S. Pat. No. 4,312,860 to Clements. Another surfactant formulation is commercially available from Ross Laboratories as SURVANTA ®, which is a natural bovine lung extract containing phospholipids, neutral lipids, fatty acids, and surfactant-associated proteins to which dipalmitoylphosphatidylcholine, palmitic acid, and tripalmitin are added to standardize the composition and to mimic surface tension lowering properties of natural lung surfactant. The surfactant formulation may be provided as a sterile lyophylized powder, which is reconstituted prior to use, or as a ready-to-use liquid.

In general, all surfactant formulations contain dipalmitoylphosphatidylcholine (DPPC; also called "Colfosceril Palmitate") as a phospholipid in an aqueous carrier, either alone or in combination with other phospholipids such as 1-palmitoyl-2-oleoylphosphatidylglycerol, dimyristoyl phosphatidylcholine, distearoyl phosphatidylcholine, dimyristoyl phosphatidylethanolamine, dilauroyl phosphatidylethanolamine, dimethyl dipalmitoyl phosphatidylcholine, methyl dipalmitoyl phosphatidylcholine, dipalmitoyl phosphatidylglycerol, phosphatidylcholine, dipalmitoyl phosphatidyl ethanolamine, dilauroyl phosphatidylcholine, dioleoyl phosphatidylcholine, and dibehenoyl phosphatidylcholine. Typically, DPPC is included in an amount from 10 to 90 mg/mL in a surfactant formulation to be nebulized and administered to the lungs.

Surfactant formulations typically have a surface tension less than 15 dynes per centimeter. Lower surface tensions (e.g., less than about 10 dynes per centimeter) tend to be preferred, with the surfactant formulations described herein being capable of providing surface tensions down to about 1 to 2 dynes per centimeter or less.

Surfactant formulations preferably include a spreading agent such as a fatty alcohol or a lung surfactant protein in an amount effective to spread the surfactant formulation on the surface of lung alveoli. In a particularly preferred embodiment of the present invention the spreading agent is cetyl alcohol (also called hexadecanol).

The aqueous phase of the surfactant formulation is preferably a saline solution (e.g., a sodium chloride solution), so as to not be unduly irritating to lung surfaces. Sodium chloride solutions may be normal saline solutions (i.e., about 0.9% NaCl), or are more preferably slightly hypotonic (e.g., about 0.4% to about 0.9% NaCl, more preferably about 0.4% to about 0.8% NaCl, and most preferably 0.54% NaCl).

Suitable surfactant formulations include those containing a lung surfactant protein as the spreading agent, as noted above. An example of such a formulation is prepared by combining a surfactant apoprotein such as described in U.S. Pat. No. 4,912,038 with a mixture of lipids, where the mixture of lipids includes DPPC, 1-palmitoyl-2-oleoyl-phosphatidylglycerol (POPG), and palmitic acid (PA), with the ratio of DPPC to POPG being from 50:50 to 90:10; with the ratio of (DPPC+POPG) to surfactant protein being from 50:1 to 5:1; and with the ratio of PA to (DPPC+POPG) being from 0 to 0.2. Other unsaturated acidic lipids than POPG may be substituted for POPG. In a particularly preferred embodiment of this type of formulation, the ratio of DPPC to POPG to PA is 7:3:1, with a final phospholipid concentration of 3 times the amount of lipid, with calcium incorporated at approximately 0.01 mg/mL to 10 mg/mL $Ca^{2+}$. See, e.g., PCT Application Publication No. WO 91/00871 of Genentech Inc. and California Biotechnology Inc. (Published Jan. 24, 1991).

The dispersion is preferably heated to a temperature between about 25° C. and 75° C., and the phospholipid is preferably dipalmitoylphosphatidylcholine (DPPC) included in an amount from about 8 to 50 milligrams per milliliter of aqueous carrier. "Heated" temperatures referred to herein are temperatures of the heating means (i.e., the heating block); the liquid surfactant formulation itself reaches a temperature somewhat lower than the heating means due to the cooling effect of nebulization). Various combinations of heating and phospholipid concentration may be employed in practicing the present invention, with the following embodiments employing DPPC being illustrative, and with the embodiment set forth in paragraph 7 below being particularly preferred:

(1) A method wherein the dispersion is heated to a temperature of about 25° C. to 55° C. and the DPPC is included in the aqueous carrier in an amount from about 30 to 50 milligrams per milliliter (mg/mL). More preferably, the dispersion is heated to a temperature of about 35° C. to 45° C. and the DPPC is included in an amount from about 35 to 45 mg/mL. Most preferably, the dispersion is heated to a temperature of about 37° C. and the DPPC is included in an amount of about 40.5 mg/mL.

(2) A method wherein the dispersion is heated to a temperature of about 45° C. to 75° C., and the DPPC is included in the aqueous carrier in an amount from about 70 to 90 mg/mL. More preferably, the dispersion is heated to a temperature of about 55° C. to 65° C. and the DPPC is included in an amount from about 75 to 85 mg/mL. Most preferably, the dispersion is heated to a temperature of about 60° C. and the DPPC is included in an amount of about 81 mg/mL.

(3) A method wherein the dispersion is heated to a temperature of about 25° C. to 55° C. and the DPPC is included in the aqueous carrier in an amount from about 70 to 90 mg/mL. More preferably, the dispersion is heated to a temperature of about 35° C. to 45° C. and the DPPC is included in an amount from about 75 to 85 mg/mL. Most preferably, the dispersion is heated to a temperature of about 37° C. and the DPPC is included in an amount of about 81 mg/mL.

(4) A method wherein the dispersion is heated to a temperature of about 45° C. to 75° C. and the DPPC is included in the aqueous carrier in an amount from about 30 to 50 mg/mL. More preferably, the dispersion is heated to a temperature of about 55° C. to 65° C. and the DPPC is included in an amount from about 35 to 45 mg/mL. Most preferably, the dispersion is heated to a temperature of about 60° C. and the DPPC is included in an amount of about 40.5 mg/mL.

(5) A method wherein the dispersion is heated to a temperature of about 25° C. to 55° C. and the DPPC is included in the aqueous carrier in an amount from about 5 to 24 mg/mL. More preferably, the dispersion is heated to a temperature of about 35° C. to 45° C. and the DPPC is included in an amount from about 8 to 20 mg/mL. Most preferably, the dispersion is heated to a temperature of about 37° C. and the DPPC is included in an amount of about 13.5 mg/mL.

(6) A method wherein the dispersion is heated to a temperature of about 45° C. to 75° C. and the DPPC is included in the aqueous carrier in an amount from about 5 to 24 mg/mL. More preferably, the dispersion is heated to a temperature of about 55° C. to 65° C. and the DPPC is included in an amount from about 8 to 20 mg/mL. Most preferably, the dispersion is heated to a temperature of about 60° C. and the DPPC is included in an amount of about 13.5 mg/mL.

(7) A method wherein the dispersion is heated to a temperature of about 45° C. to 75° C. and the DPPC is included in the aqueous carrier in an amount from about 5 to 24 milligrams per milliliter (mg/mL). More preferably, the dispersion is heated to a temperature of about 45° C. to 55° C., and the DPPC is included in an amount of from about 8 to 20 mg/mL. Most preferably, the dispersion is heated to a temperature of about 50° C. and the DPPC is included in an amount of about 13.5 mg/mL.

(8) A method wherein the dispersion is heated to a temperature of about 45° C. to 75° C. and the DPPC is included in the aqueous carrier in an amount from about 30 to 50 mg/mL. More preferably, the dispersion is heated to a temperature of about 45° C. to 55° C., and the DPPC is included in an amount of from about 35 to 45 mg/mL. Most preferably, the dispersion is heated to a temperature of about 50° C. and the DPPC is included in an amount of about 40.5 mg/mL.

(9) A method wherein the dispersion is heated to a temperature of about 45° C. to 75° C., and the DPPC is included in the aqueous carrier in an amount from about 70 to 90 mg/mL. More preferably, the dispersion is heated to a temperature of about 45° C. to 55° C., and the DPPC is included in an amount of from about 75 to 85 mg/mL. Most preferably, the dispersion is heated to a temperature of about 50° C. and the DPPC is included in an amount of about 81 mg/mL.

In general, the dispersion is heated to a temperature of at least about the transition temperature of the phospholipid. Note that nebulization of the surfactant formulation causes the temperature of that formulation to drop, so heating the formulation will be required to maintain the temperature of the surfactant formulation even at room temperature during continuous nebulization.

Respirable surfactant particles may be delivered to a patient by any suitable means, including spontaneous inhalation and mechanical ventilation. In spontaneous inhalation, the patient inhales the surfactant particles. Numerous different aerosol inhalers are known. The term "ventilation" herein refers to the process of cyclically forcing oxygen-rich air into, and permitting oxygen-depleted air to escape from, at least one lung of a patient to assist the breathing of the patient or to breath for the patient when the patient would not otherwise breath on its own. Ventilation may be of either or both lungs of a patient, depending on whether any one lung is blocked, collapsed, or otherwise inoperable. Numerous types of ventilating apparatus are known. When respirable particles are to be administered to a particles by ventilation, the respirable particles are typically generated by means of a nebulizer, with the nebulizer output combined with or delivered to the ventilator output for ultimate delivery to the patient. The nebulizer can load the ventilator during the inhalation phase or exhalation phase of the ventilator cycle.

Any nebulizing apparatus capable of forming respirable particles (e.g, particles from 1 to 10 microns volume meadian diameter in size) from a surfactant formulation as described above may be employed in practicing the present invention, including both jet nebulizers and ultrasonic nebulizers. Those skilled in the art will appreciate that the aerosol produced by the nebulizing apparatus may contain larger particles which are not respirable, so long as a sufficient quantity of respirable particles are included in the aerosol to accomplish the intended purpose. An example jet nebulizer is described in U.S. Pat. No. 4,832,012. Example ultrasonic nebulizers include the Porta-Sonic™ and the Pulmo-Sonic™ nebulizers produced by The DeVilbiss Co., Somerset, Pa., USA.

The present invention is explained in greater detail in the examples set forth below. In the examples, "cc" means cubic centimeter, "g" means grams, "mg" means milligrams, "mL" means milliliter, "psi" means pounds per square inch, "mOsm⇄ means milliosmoles, "N" means normal, "L" means liter, "min" means minutes, "hr" means hour, percentages are given on a by-weight basis, "Amb" means ambient, and temperatures are given in degrees Centigrade unless otherwise indicated.

EXAMPLE 1

Preparation of Surfactant Formulation 25 cc of sterile, pyrogen-free water is taken up in a sterile disposable syringe and injected into a sterile, evacuated, 50 cc vial containing a lyophilized powder of 2.025 g dipalmitoylphosphatidylcholine (DPPC), 225 mg hexadecanol, 150 mg tyloxapol, and 876.6 mg NaCl. This mixture is known. See U.S. Pat. No. 4,826,821 to Clements. The water and powder are vigorously mixed by inverting the vial and repeatedly withdrawing the mixture into the syringe and releasing the plunger of the syringe. The result is approximately 25 cc of surfactant formulation, which is a suspension rather than a solution. The formulation is placed in a nebulizer well and diluted as needed with 125 mL of sterile pyrogen free water. The resulting surfactant formulation is 0.1N with respect to NaCl, has an osmolality of 190 mOsm/1, and contains 13.5 mg/cc of DPPC, 1.5 mg/cc of hexadecanol, and 1 mg/cc of tyloxapol. This formulation is referred to below as a 1× surfactant formulation. A 3× and 6× surfactant formulation is prepared in essentially the same manner, except that the DPPC, hexadecanol, and tyloxapol are increased three and six times by weight, respectively. NaCl is maintained at approximately a 0.1 N concentration in the 3× and 6× formulations.

EXAMPLE 2

Test Apparatus

A test apparatus was assembled from a SERVO 900C ventilator (Siemens-Elema AB, Sweden) and a VISAN™ nebulizer unit (Vortran Medical Technology ,Inc., Sacramento, Calif.). Compressed air (50 psi) was supplied to an oxygen/air blender and used to supply gas to both the ventilator and the nebulizer, with the nebulizer gas supply passing through a separate nebulizer flowmeter. The nebulizer control unit was electrically connected to the electrical signal source of the respirator which controls the inhalation phase of the breathing cycle so that nebulized surfactant was delivered intermittently, during the inhalation phase of the ventilator respiratory function. The ventilator and nebulizer output were each connected to a patient Y tube, which was in turn connected to a 7 foot section of TYGON™ tubing (R-3603, ⅜" i.d.) coiled inside of a 4 liter Ehrlenmeyer filter flask. The output of the filter flask was connected to a second 7 foot section of TYGON™ tubing which was coiled inside a second 4 liter Ehrlenmeyer filter flask. The coiled tubing served as artificial lungs to collect the nebulized surfactant formulation. The filter flasks were sealed with latex gloves and placed in methanol/dry ice baths prior to each experiment. The bath temperature was regulated during the experiment to avoid collection tube occlusion caused by freezing.

The ventilator and nebulizer unit were set to deliver a combined total inspiratory tidal volume ($V_t$) of 750 mL/breath. Initial tidal volumes were checked by installing a rubber "lung" at the patient Y tube and observing the appropriate ventilator gauges. Ventilator mean airway pressure (cm water) was monitored and recorded initially and at each sampling time to determine the back pressure on the system. Instrument settings for the ventilator and nebulizer unit were as follows: The ventilator was set to a Working pressure of 70 cm water; a breathing rate (f) of 20 breaths/min; an inhalation fraction ($P_i$) of 25%; and an Inspiratory Minute Volume (MV) of 7.5 L/min. The nebulizer was set to a working pressure of 50 psi; a flow rate (from flowmeter) of 30 L/min; and a flow rate (from nebulizer) of 500 mL/sec (2 nebulizer jets open).

EXAMPLE 3

Nebulization of Surfactant Formulations at Ambient and Ice Bath Temperatures

A total of 18 experiments were performed utilizing the parameters listed in Table 1 (subsequent Tables refer to Table 1 for the definition of experiments).

TABLE 1

Experimental Parameters

| Experiment Number | Surfactant Preparation | Delivery Tube Length (feet) | Nebulizer Bath Temperature |
|---|---|---|---|
| A | 1X | 4 | ice |
| B | 1X | 0.5 | ice |
| C | 1X | 2 | ice |
| D | 3X | 4 | ice |
| E | 3X | 0.5 | ice |
| F | 3X | 2 | ice |
| G | 6X | 4 | ice |
| H | 6X | 0.5 | ice |
| I | 6X | 2 | ice |
| J | 1X | 4 | ambient |
| K | 1X | 0.5 | ambient |
| L | 1X | 2 | ambient |
| M | 3X | 4 | ambient |
| N | 3X | 0.5 | ambient |
| O | 3X | 2 | ambient |
| P | 6X | 4 | ambient |
| Q | 6X | 0.5 | ambient |
| R | 6X | 2 | ambient |

Variables included the surfactant formulation concentration (1X, 3X, 6X), the nebulizer—Y delivery tube length, the nebulization bath temperature (ice water temperature at about 2° C., or ambient temperature at about 22° C.), and nebulization time. Samples taken from the nebulizer and collection flasks were removed at 2, 4, and 6 hours after beginning nebulization. Nebulizers were weighed initially and upon completion of the experiment to determine the total amount of surfactant nebulized by weight. The collection flasks were removed from the ventilator circuit at predetermined sampling times, allowed to equilibrate to room temperature, and subsequent sets of cooled flasks installed immediately following removal. The total volume of collected material was measured and then combined with a 150-mL distilled water rinse of the flasks and Tygon tubing. The collected and rinse fractions were combined, mixed, and equal portions aliquoted into four 50-mL glass vials.

Nebulizer samples were obtained by removing 10-mL fraction from the nebulizer at each sampling time. Three 3-mL portions of the nebulizer fraction were then transferred to 10-mL glass vials. Both the collected and nebulizer samples were lyophilized using a Virtis freeze dryer for 3-4 days.

The Tygon tubing and flasks were thoroughly rinsed with hot and distilled water and allowed to dry after each sampling period. The nebulizer and ventilator tubing were replaced after each experiment.

The lyophilized samples were dissolved in either methanol or chloroform, diluted appropriately according to their initial concentration, and tested (a) for DPPC concentration by HPLC analysis, (b) for Tyloxapol concentration by UV determination, and (c) for cetyl alcohol concentration by GC analysis.

The relative weight loss from nebulization (which can be related to efficiency) determinations from the initial and final weights are contained in Table 2. Note that the weight loss numbers include the 30 mL of liquid taken from the nebulizer for sampling purposes. Although this fraction was not aerosolized, the amount removed was constant for each experiment. The weight loss determinations can therefore be used for comparison for the experimental variables.

TABLE 2

Relative Weight Loss From Nebulization

| Experiment Number | % Weight Loss | Mean |
|---|---|---|
| A | 60.1 | 61.1 |
| B | 62.9 | |
| C | 60.2 | |
| D | 58.2 | 51.5 |
| E | 48.3 | |
| F | 48.1 | |
| G | 61.6 | 55.4 |
| H | 49.1 | |
| I | 55.4 | |
| J | 73.0 | 73.1 |
| K | 80.9 | |
| L | 65.3 | |
| M | 61.1 | 57.5 |
| N | 52.7 | |
| O | 58.6 | |
| P | 62.7 | 61.4 |
| Q | 56.4 | |
| R | 65.0 | |

Table 3 lists collection flask volumes recovered from the experiments. The experiments are grouped by the surfactant formulation reconstitution strength (1X, 3X, or 6X). There were no trends in the data to suggest delivery tube length had any significant effect on the volume or mass of surfactant formulation collected. There were also no significant differences in results determined for the 2, 4, and 6 hour collection times. Therefore, to simplify examination of the data, averages of values for collected tube lengths and total amount collected are presented for 1X, 3X, and 6X concentrations at ice or ambient temperature. Collected fraction total mass determinations are presented in Tables 4-7.

TABLE 3

| | Collected Volumes (mL) | | | |
|---|---|---|---|---|
| Experiment Number | 2 Hour | 4 Hour | 6 Hour | Total mL Collected |
| A* | 19 | 22 | 17 | 58 |
| B | 14 | 17 | 12 | 43 |
| C | 17 | 17 | 15 | 49 |
| D | 12 | 21 | 20 | 53 |
| E | 14 | 19 | 9 | 42 |
| F | 17 | 14 | 14 | 45 |
| G* | 19 | 19 | 21 | 59 |
| H* | 18 | 10 | 5 | 33 |
| I | 19 | 15 | 14 | 48 |
| J | 20 | 10 | 25 | 55 |

TABLE 3-continued

| | Collected Volumes (mL) | | | |
|---|---|---|---|---|
| Experiment Number | 2 Hour | 4 Hour | 6 Hour | Total mL Collected |
| K* | 21 | 19 | 17 | 57 |
| L | 18 | 16 | 17 | 51 |
| M | 18 | 26 | 17 | 61 |
| N | 22 | 27 | 19 | 68 |
| O | 23 | 22 | 14 | 59 |
| P | 18 | 20 | 18 | 56 |
| Q | 19 | 20 | 17 | 56 |
| R | 25 | 19 | 20 | 64 |

*Mean of 2 Experiments

TABLE 4

Collected Fractions - DPPC Determinations

| Surfactant Formulation | Nebulizer Bath | Initial Nebulizer Concentration mg/mL | Mean Total Mass (mg) | Mean Total Volume (mL) |
|---|---|---|---|---|
| 1X | Ice | 13.5 | 128.1 | 50.0 |
| 3X | Ice | 40.5 | 412.8 | 46.7 |
| 6X | Ice | 81.0 | 894.9 | 46.7 |
| 1X | Amb | 13.5 | 217.7 | 54.3 |
| 3X | Amb | 40.5 | 665.6 | 62.7 |
| 6X | Amb | 81.0 | 1341.5 | 58.7 |

TABLE 5

Collected Fractions - Tyloxapol Determinations

| Surfactant Formulation | Nebulizer Bath | Initial Nebulizer Concentration mg/mL | Mean Total Mass (mL) | Mean Total Volume (mL) |
|---|---|---|---|---|
| 1X | Ice | 1.0 | 19.4 | 50.0 |
| 3X | Ice | 3.0 | 51.2 | 46.7 |
| 6X | Ice | 6.0 | 91.2 | 46.7 |
| 1X | Amb | 1.0 | 27.5 | 54.3 |
| 3X | Amb | 3.0 | 81.5 | 62.7 |
| 6X | Amb | 6.0 | 138.1 | 58.7 |

TABLE 6

Collected Fractions - Cety Alcohol Determinations

| Surfactant Formulation | Nebulizer Bath | Initial Nebulizer Concentration mg/mL | Mean Total Mass (mg) | Mean Total Volume (mL) |
|---|---|---|---|---|
| 1X | Ice | 1.5 | 12.1 | 50.0 |
| 3X | Ice | 4.5 | 40.4 | 46.7 |
| 6X | Ice | 9.0 | 77.3 | 46.7 |
| 1X | Amb | 1.5 | 21.1 | 54.3 |
| 3X | Amb | 4.5 | 62.7 | 62.7 |
| 6X | Amb | 9.0 | 144.4 | 58.7 |

TABLE 7

Collected Fractions - Sodium Chloride Determinations

| Surfactant Formulation | Nebulizer Bath | Initial Nebulizer Concentration mg/mL | Mean Total Mass (mg) | Mean Total Volume (mL) |
|---|---|---|---|---|
| 1X | Ice | 5.8 | 61.3 | 50.0 |
| 3X | Ice | 5.2 | 67.6 | 46.7 |
| 6X | Ice | 5.8 | 77.1 | 46.7 |
| 1X | Amb | 5.8 | 104.7 | 54.3 |
| 3X | Amb | 5.2 | 100.3 | 62.7 |
| 6X | Amb | 5.8 | 117.6 | 58.7 |

Analysis of Tables 2-7 above indicate that nebulization efficiency by weight, collected volumes, and collected mass determinations are higher using ambient nebulizer baths (Experiments J-R) as compared to the ice water nebulizer baths (Experiments A-I).

EXAMPLE 4

Nebulization of Surfactant Formulations at 37 Degrees Centigrade

This experiment was undertaken to investigate surfactant nebulization at 37° C. The apparatus employed was essentially the same as described in Example 2 above, except that a Brinkman IC-2 immersion heater/-circulator was used with the nebulizer bath. Duplicate experiments were performed at 37° for 1×, 3×, and 6× surfactant formulation concentrations. Experimental conditions were essentially the same as described in Example 2 above, except that (a) a 4 foot delivery tube length was utilized for all the experiments; the nebulizer bath temperature was maintained at 37° C.; (c) the nebulizer was initially filled with 200mL of the respective surfactant formulation (as opposed to 150mL in Example 2); (d) an additional 50mL of the surfactant formulation was added to the nebulizer after the 4 hour collection period for the 3× and 6× experiments; (e) rinse volumes for the collection vessels and Tygon tubing were decreased to 50mL for each flask and tubing (compared to 75mL in the previous study); and (f) testing of the collected+rinse fractions for DPPC was done directly on methanol dilutions of the samples rather than after lyophylization. The increased initial nebulizer volume and the addition of 50mL of surfactant formulation at 4 hours were implemented to maintain sufficient levels of the reconstituted drug in the nebulizer. Rinse volumes were decreased to concentrate the surfactant formulation constituents in the rinse plus collected sample fractions.

Summarized results are presented in Table 8 along with the values previously obtained for analogous experiments (4 foot delivery tubes) at ice and ambient temperatures in Example 3 above. Where experiments have been repeated, data has been pooled. Both collected volumes and total DPPC mass were increased compared to the values obtained in the earlier ice and ambient studies. FIGS. 1-3 illustrate the mean total mass of DPPC recovered as a function of nebulizer bath temperature. Bath temperature values used were ice (2° C.), ambient (22° C.), and heated (37° C.). The results indicate increased DPPC total mass was delivered with increased nebulizer bath temperatures.

TABLE 8

Collected Fractions - DPPC Determinations

| Surfactant Formulation | Nebulizer Bath | Initial Nebulizer Concentration mg/mL | Mean Total Mass (mg) | Mean Total Volume (mL) |
|---|---|---|---|---|
| 1X | Ice | 13.5 | 119 | 58 |
| 1X | Ambient | 13.5 | 215 | 55 |
| 1X | 37° C. | 13.5 | 385 | 112 |
| 3X | Ice | 40.5 | 604 | 53 |
| 3X | Ambient | 40.5 | 719 | 61 |
| 3X | 37° C. | 40.5 | 1513 | 101 |
| 6X | Ice | 81.0 | 1012 | 58 |
| 6X | Ambient | 81.0 | 1274 | 56 |
| 6X | 37° C. | 81.0 | 988 | 80 |

EXAMPLE 5

Nebulization of Surfactant Formulations at 60 Degrees Centigrade

This experiment was undertaken to investigate the nebulization of surfactant formulation at 60° C. utilizing an apparatus and experimental parameters as described in Example 4 above.

Figure 4:
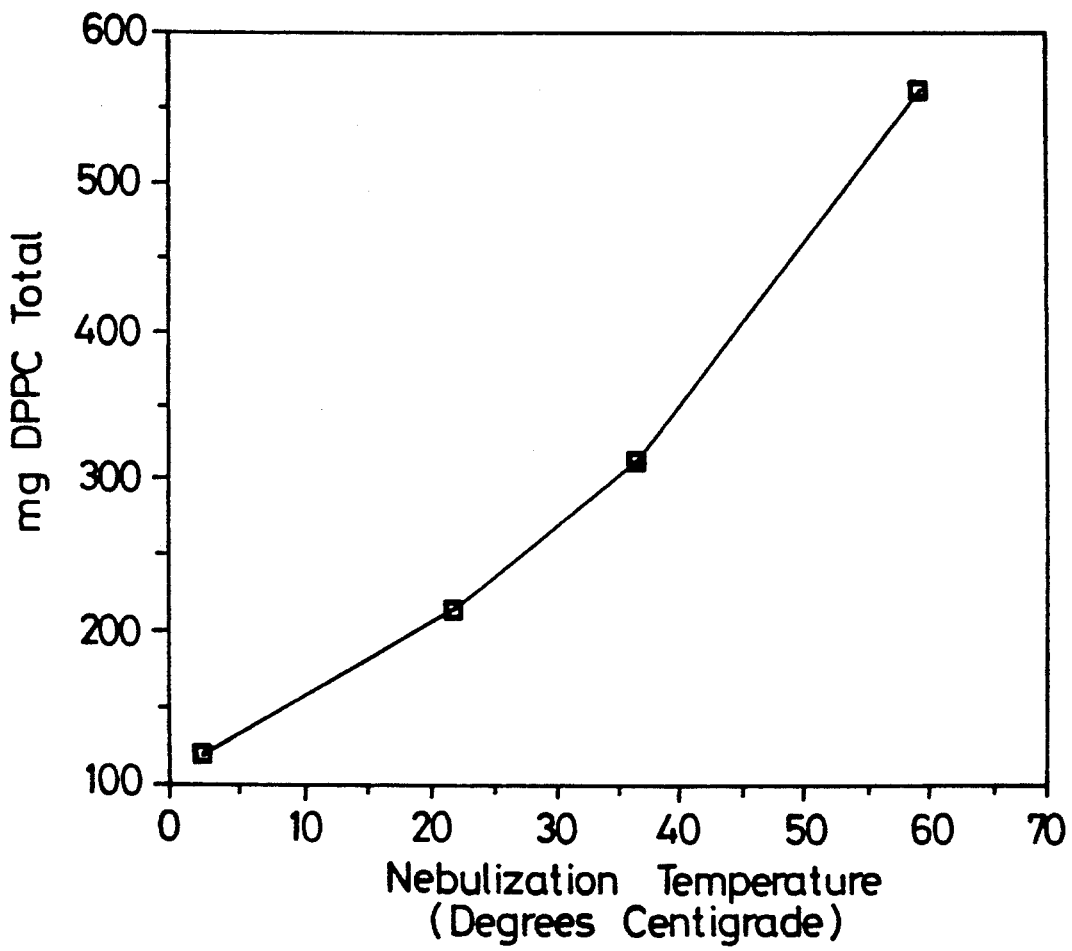
FIG. 4 shows total mg of DPPC collected from a nebulized 1× surfactant formulation maintained at temperatures ranging from 2° C. to 60° C.
Figure 5:
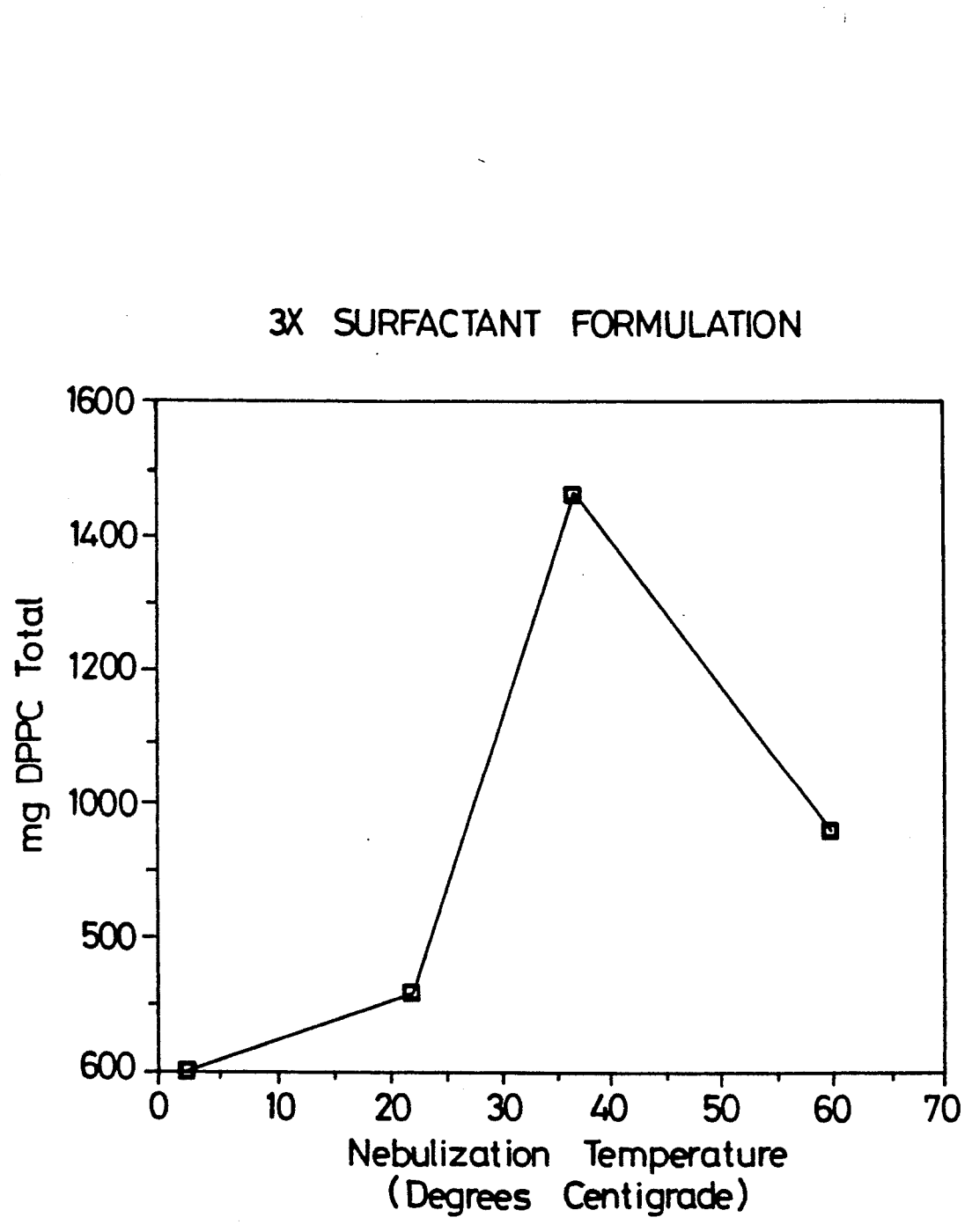
Figure 6:
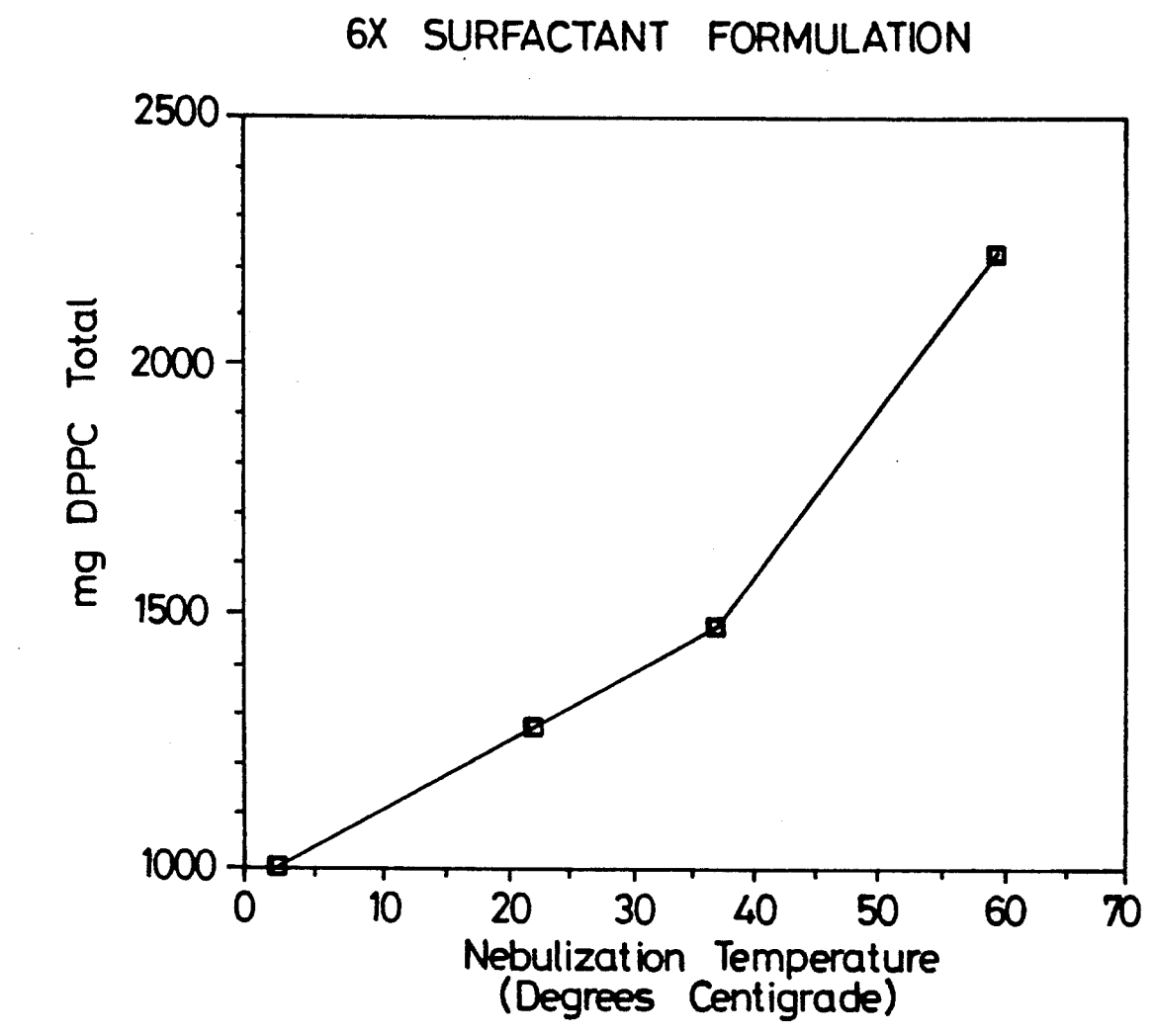

Summarized results are presented in Table 9 along with the values previously obtained for analogous experiments (4 foot delivery tubes) at ice, ambient and 37° temperatures as described in Examples 3 and 4 above. Where experiments have been repeated, data has been pooled. FIGS. 4–6 illustrate the mean total mass of DPPC recovered as a function of nebulizer bath temperature. These data indicate the total DPPC deliveries for the 1× and 6× reconstitutions were significantly increased as compared to the results obtained for analogous experiments at ice, ambient, and 37° C. temperatures.

Surprisingly, the 3× surfactant formulation showed a decrease in DPPC delivery at the 60° C. nebulization temperature as compared to that found in the 37° C. experiment. The mechanism producing this effect is unknown.

TABLE 9

Collected Fractions - DPPC Determinations

| Surfactant Formulation | Nebulizer Bath | Initial Nebulizer Concentration mg/mL | Mean Total Mass (mg) | Mean Total Volume (mL) |
|---|---|---|---|---|
| 1X | Ice | 13.5 | 119 | 58 |
| 1X | Amb | 13.5 | 215 | 55 |
| 1X | 37° C. | 13.5 | 385 | 112 |
| 1X | 60° | 13.5 | 562 | 115 |
| 3X | Ice | 40.5 | 604 | 53 |
| 3X | Amb | 40.5 | 719 | 61 |
| 3X | 37° C. | 40.5 | 1513 | 101 |
| 3X | 60° | 40.5 | 947 | 109 |
| 6X | Ice | 81.0 | 1012 | 58 |
| 6X | Amb | 81.0 | 1274 | 56 |
| 6X | 37° C. | 81.0 | 988 | 80 |
| 6X | 60° | 81.0 | 2045 | 79 |

The invention comprises any novel feature or combination of features disclosed herein, including, but not limited to, the following.

We claim:

1. A method of administering a surfactant dispersion to the lungs of a patient in need of such treatment, comprising:
   providing a dispersion comprised of a phospholipid dispersed in an aqueous carrier; wherein said phospholipid is dipalmitoylphosphatidylcholine (DPPC); and wherein said DPPC is included in an amount from about 10 to 90 milligrams per milliliter of aqueous carrier; then
   heating the dispersion to a temperature between about 25° C. and 90° C.; then
   nebulizing the dispersion to respirable surfactant particles; and then
   delivering the respirable surfactant particles to the lungs of a patient.

2. A method according to claim 1, wherein said dispersion is heated to a temperature of at least about the transition temperature of said phospholipid.

3. A method according to claim 1, wherein said dispersion is heated to a temperature between about 25° C. and 75° C.

4. A method according to claim 1, wherein said DPPC is included in an amount from about 8 to 50 milligrams per milliliter of aqueous carrier.

5. A method according to claim 1, wherein said surfactant dispersion further includes a spreading agent; and wherein said surfactant dispersion has a surface tension less than 15 dynes per centimeter.

6. A method according to claim 5, wherein said spreading agent is a fatty alcohol.

7. A method according to claim 5, wherein said spreading agent is cetyl alcohol.

8. A method according to claim 5, wherein said spreading agent is a lung surfactant protein.

9. A method according to claim 1, wherein said respirable particles are delivered by ventilation.

10. A method according to claim 1, wherein said respirable particles are from about 1 to 10 microns in size.

11. A method according to claim 1, wherein said nebulizing step is carried out with a jet nebulizer.

12. A method according to claim 1, wherein said dispersion is heated to a temperature of about 25° C. to 55° C. and said DPPC is included in said aqueous carrier in an amount from about 5 to 24 mg/mL.

13. A method according to claim 12, wherein said dispersion is heated to a temperature of about 35° C. to 45° C. and said DPPC is included in an amount from about 8 to 20 mg/mL.

14. A method according to claim 13, wherein said dispersion is heated to a temperature of about 37° C. and said DPPC is included in an amount of about 13.5 mg/mL.

15. A method according to claim 1, wherein said dispersion is heated to a temperature of about 45° C. to 75° C. and said DPPC is included in said aqueous carrier in an amount from about 5 to 24 mg/mL.

16. A method according to claim 15, wherein said dispersion is heated to a temperature of about 55° C. to 65° C. and said DPPC is included in an amount from about 8 to 20 mg/mL.

17. A method according to claim 16, wherein said dispersion is heated to a temperature of about 60° C. and said DPPC is included in an amount of about 13.5 mg/mL.

18. A method of administering a surfactant dispersion to the lungs of a patient in need of such treatment, comprising:
   providing a dispersion comprised of a phospholipid dispersed in an aqueous carrier; wherein said phospholipid is dipalmitoylphosphatidylcholine (DPPC); wherein said DPPC is included in an amount from about 30 to 90 milligrams per milliliter of aqueous carrier; wherein said surfactant dispersion further includes a spreading agent; and wherein said surfactant dispersion has a surface tension less than 15 dynes per centimeter; then
   heating the dispersion to a temperature between about 25° C. and 75° C.; then
   nebulizing the dispersion to respirable surfactant particles; and then
   delivering the respirable surfactant particles to the lungs of a patient.

19. A method according to claim 18, wherein said dispersion is heated to a temperature of about 25° C. to 55° C., and wherein said DPPC is included in said aqueous carrier in an amount from about 30 to 50 milligrams per milliliter.

20. A method according to claim 19, wherein said dispersion is heated to a temperature of about 35° C. to 45° C., and wherein said DPPC is included in said aqueous carrier in an amount from about 35 to 45 milligrams per milliliter.

21. A method according to claim 20, wherein said dispersion is heated to a temperature of about 37° C., and wherein said DPPC is included in said aqueous carrier in an amount of about 40.5 milligrams per milliliter.

22. A method according to claim 18, wherein said dispersion is heated to a temperature of about 45° C. to 75° C., and wherein said DPPC is included in said aqueous carrier in an amount from about 70 to 90 milligrams per milliliter.

23. A method according to claim 22, wherein said dispersion is heated to a temperature of about 55° C. to 65° C., and wherein said DPPC is included in said aqueous carrier in an amount from about 75 to 85 milligrams per milliliter.

24. A method according to claim 23, wherein said dispersion is heated to a temperature of about 60° C., and wherein said DPPC is included in said aqueous carrier in an amount of about 81 milligrams per milliliter.

25. A method according to claim 18, wherein said dispersion is heated to a temperature of about 25° C. to 55° C., and wherein said DPPC is included in said aqueous carrier in an amount from about 70 to 90 milligrams per milliliter.

26. A method according to claim 25, wherein said dispersion is heated to a temperature of about 35° C. to 45° C., and wherein said DPPC is included in said aqueous carrier in an amount from about 75 to 85 milligrams per milliliter.

27. A method according to claim 26, wherein said dispersion is heated to a temperature of about 37° C., and wherein said DPPC is included in said aqueous carrier in an amount of about 81 milligrams per milliliter.

28. A method according to claim 18, wherein said dispersion is heated to a temperature of about 45° C. to 75° C., and wherein said DPPC is included in said aqueous carrier in an amount from about 30 to 50 milligrams per milliliter.

29. A method according to claim 28, wherein said dispersion is heated to a temperature of about 55° C. to 65° C., and wherein said DPPC is included in said aqueous carrier in an amount from about 35 to 45 milligrams per milliliter.

30. A method according to claim 29, wherein said dispersion is heated to a temperature of about 60° C., and wherein said DPPC is included in said aqueous carrier in an amount of about 40.5 milligrams per milliliter.

31. A method according to claim 18, wherein said spreading agent is a fatty alcohol.

32. A method according to claim 18, wherein said spreading agent is cetyl alcohol.

33. A method according to claim 18, wherein said spreading agent is a lung surfactant protein.

34. A method according to claim 18, wherein said respirable particles are delivered by ventilation.

35. A method according to claim 18, wherein said respirable particles are from about 1 to 10 microns in size.

36. A method according to claim 18, wherein said nebulizing step is carried out with a jet nebulizer.

* * * * *